United States Patent [19]

Hebbard et al.

[11] Patent Number: 5,476,711
[45] Date of Patent: Dec. 19, 1995

[54] FIBER BLENDING SYSTEM

[75] Inventors: Carl Hebbard, Federal Way; Lee E. Perdelwitz, Jr., Tacoma; Paul G. Gaddis, Renton, all of Wash.

[73] Assignee: Weyerhaeuser Company, Tacoma, Wash.

[21] Appl. No.: 221,024

[22] Filed: Mar. 30, 1994

Related U.S. Application Data

[62] Division of Ser. No. 603,336, Oct. 25, 1990, Pat. No. 5,316,601.

[51] Int. Cl.$^6$ .......................... B32B 31/06; B32B 31/26; D04H 1/54; D04H 1/70
[52] U.S. Cl. .......................... 428/283; 19/145.5; 19/305; 156/62.4; 156/308.2; 264/112; 264/116; 264/122; 264/126; 428/286; 428/287; 428/296
[58] Field of Search ................................. 19/145.5, 305; 264/112, 116, 122, 126; 156/62.4, 308.2; 428/283, 286, 287, 296

[56] References Cited

U.S. PATENT DOCUMENTS

| | | |
|---|---|---|
| 731,764 | 6/1903 | Fordyce . |
| 2,152,901 | 4/1939 | Manning . |
| 2,543,101 | 2/1951 | Francis, Jr. . |
| 2,757,150 | 7/1956 | Heritage . |
| 2,940,135 | 6/1960 | Heritage . |
| 2,953,187 | 9/1960 | Francis . |
| 3,010,161 | 11/1961 | Duvall . |
| 3,016,582 | 1/1962 | Joa . |
| 3,035,219 | 7/1963 | Cumbers . |
| 3,136,649 | 6/1964 | Keahey, Jr. . |
| 3,973,291 | 8/1976 | Kolbach . |
| 4,129,132 | 12/1978 | Butterworth et al. . |
| 4,241,881 | 12/1980 | Laumer . |
| 4,315,347 | 2/1982 | Austin et al. . |
| 4,366,111 | 12/1982 | Dinius et al. . |
| 4,382,758 | 5/1983 | Nopper et al. . |
| 4,425,126 | 1/1984 | Butterworth et al. . |
| 4,495,119 | 1/1985 | Chung . |
| 4,784,892 | 11/1988 | Storey et al. . |
| 4,813,948 | 3/1989 | Insley . |
| 4,900,377 | 2/1990 | Redford et al. . |

FOREIGN PATENT DOCUMENTS

| | | |
|---|---|---|
| 529570 | 6/1983 | Australia . |
| 0294137 | 12/1988 | European Pat. Off. . |
| 69287 | 10/1969 | Germany . |
| 2516373 | 10/1975 | Germany . |
| 1143937 | 2/1969 | United Kingdom . |
| 2061339 | 5/1981 | United Kingdom . |

OTHER PUBLICATIONS

Dan Web Former System shown on Appendix "A" Figures 1, 2 and 3.
M & J Web Former System shown on Appendix "A" Figure 4.
International Search Report, PCT/US91/07229.

*Primary Examiner*—James C. Cannon
*Attorney, Agent, or Firm*—Klarquist Sparkman Campbell Leigh & Whinston

[57] ABSTRACT

A fiber blending system includes an apparatus and method of forming a mat of cellulosic fibers and synthetic fibers, as well as a mat thereby formed. The method includes the steps of fiberizing cellulosic material into cellulosic fibers in a fiberizer, volumetrically metering a metered amount of synthetic fibers, and injecting the metered amount of synthetic fibers into the cellulosic fibers. The cellulosic fibers are blended with the metered amount of synthetic fibers in a blending chamber to form a fiber blend. The fiber blend is dispersed through a fiber disperser having apertures of a preselected size and shape to provide a dispersed fiber blend. A third type of fiber may also be mixed with the dispersed fiber blend. The dispersed fiber blend is collected as a mat on a fiber collector to provide a mat of blended cellulosic and synthetic fibers. The mat may be thermobonded by a thermobonder and sandwiched between a facing sheet and a backing sheet. By varying the aperture preselection, as well as the size and type of fibers, a bonded mat having desired mat characteristics is formed.

8 Claims, 2 Drawing Sheets

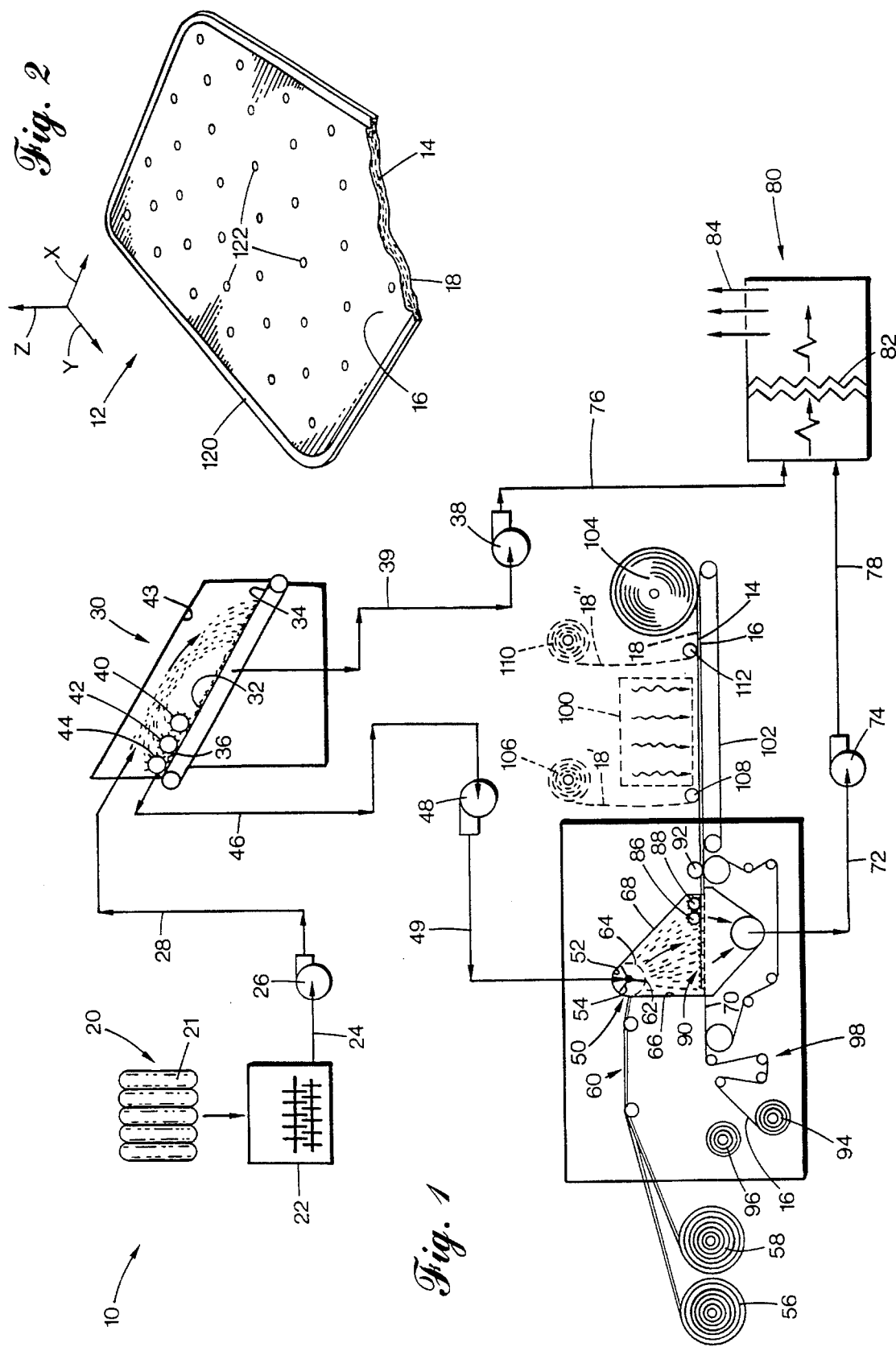

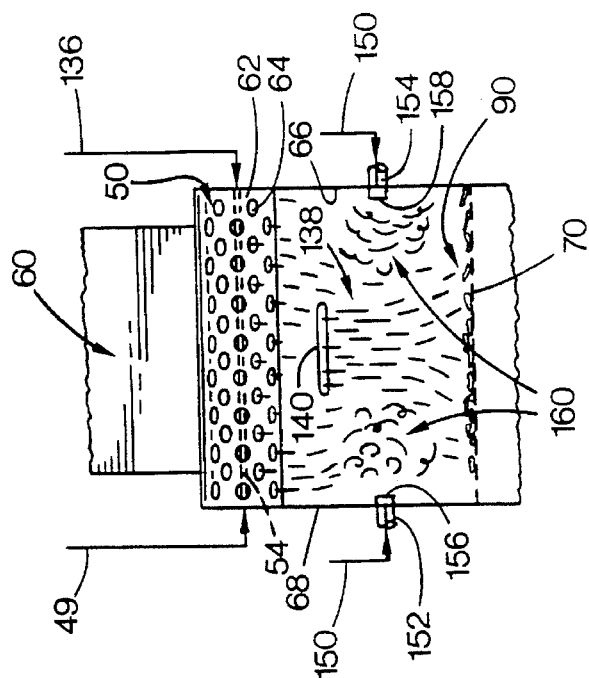
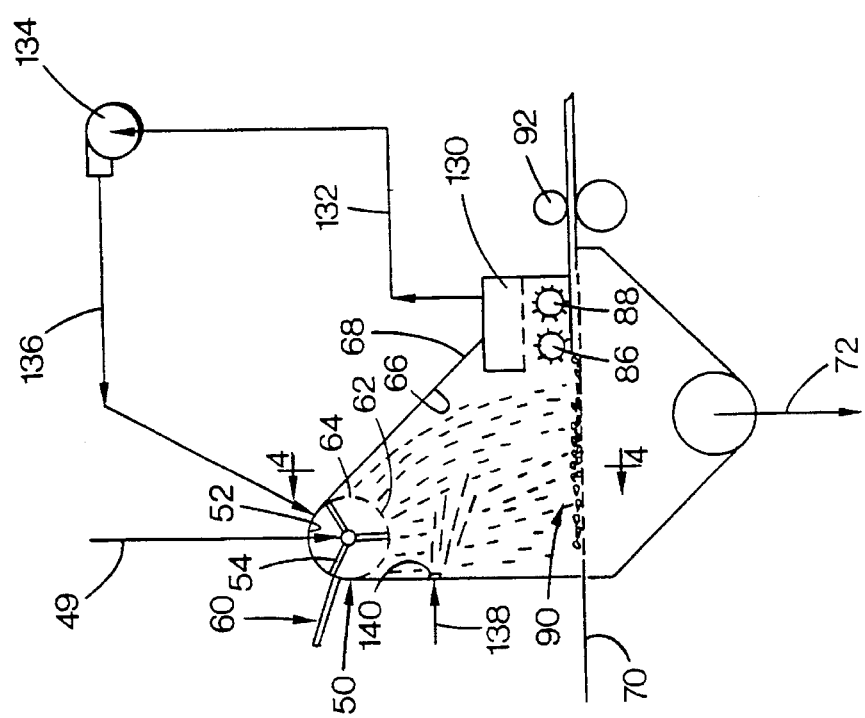

FIBER BLENDING SYSTEM

This is a division of application Ser. No. 07/603,336, filed Oct. 25, 1990, now U.S. Pt. No. 5,316,601.

BACKGROUND OF THE INVENTION

The present invention relates generally to a method of making articles containing cellulosic fibers, such as wood pulp, and synthetic fibers. More specifically, the invention relates to an apparatus for and a method of continuously feeding and blending cellulosic and synthetic fibers in a metered fashion to create a homogeneous blend which may be air-layed and thermobonded, as well as to an article formed in this manner.

Although methods of blending cellulosic and synthetic fibers and other fibers are known, these prior methods, and articles produced by such methods, suffer from a number of disadvantages. Uncontrolled blending of synthetic fibers with cellulosic fibers results in an inconsistent blend producing variances in the properties of a given article, as well as variances between articles. For example, stratification of the air-layed blend, where the cellulosic fibers are layered separately from the synthetic fibers, may result in nonuniform heat bonding of a core formed by the cellulosic and synthetic fibers. Therefore, strict quality control and product uniformity in such areas as basis weight, and strength are hampered by these earlier known methods.

Furthermore, the known methods of blending fibers suffer from problems associated with producing a wide variety of closely controlled blend ratios of cellulosic to synthetic fibers. Moreover, these methods experience problems when simultaneously blending several fibers of different lengths, deniers or superabsorbent polymers (SAP). Additionally, earlier methods of blending known to the inventors cannot be effectively controlled so as to provide a resulting article with either high X–Y tensile strength, high Z-tensile strength, or a combination thereof.

Two known earlier fiber blending systems are known as a Dan Web Former and a M & J Web Former. The Dan and M & J Web Formers are modifications of an earlier system, known as the Kroyer Process, which dealt with a method of air-laying dry cellulose fibers.

The Dan Web Former has a pulp preparation line preparing wood pulp fibers, and a synthetic fiber preparation line preparing synthetic fibers, with the wood pulp fibers and synthetic fibers being mixed within a distribution head drum. The pulp preparation line includes a hammermill which receives and fiberizes wood pulp sheets in a fiberizing chamber. The hammermill has a fiberization screen at the exit of the fiberization chamber for determining the degree of wood pulp fiberization, that is the size of the wood pulp fibers. The wood pulp fibers are delivered through a blower from the hammermill to the interior of the distribution head drum.

The Dan Web Former synthetic fiber preparation line has a fiber opening system which receives and opens synthetic fiber bales. The opened synthetic fibers are metered by weight, not volume, and then are forced with another blower to the interior of the distribution head drum. The distribution head drum has a plurality of apertures extending through the drum wall. The drum is rotated about its longitudinal axis, and has several cylindrical combers in the drum which aid in mixing the fibers and pushing them through the holes in the drum wall. The drum is supported from below by at least two rollers, which serve to rotate the drum. The drum is surrounded by a shroud and a foraminous conveyer belt passes through the shroud beneath the drum. A vacuum may be pulled within the shroud to draw the fibers onto the foraminous conveyer belt.

The Dan Web Former distribution head drum serves as a tumble mixer and a sifter, with the synthetic and wood pulp fibers eventually sifting through the holes in the drum wall. In commercial practice, with drum wall holes ¼ inch in diameter, the length of fibers which fall through the distribution head are not longer than ¼ inch. If the drum wall holes are enlarged, the fibers fall through before substantial mixing has taken place, resulting in a nonuniform blend of synthetic and pulp fibers. Furthermore, the resulting mat has a nonuniform mat thickness.

The M & J Web Former has a pulp preparation line and a synthetic fiber preparation line similar to that discussed above for the Dan Web Former. For mixing the wood pulp and synthetic fibers, the M & J Web Former has an enclosed housing with a plurality of rotary props mounted therein. The enclosed housing has a foraminous conveyer belt running therethrough, with a vacuum being drawn beneath the foraminous conveyer. The synthetic fibers and pulp fibers are blown into an upper region of the housing. The rotary propellers or props are suspended from an upper housing wall, and rotate to create turbulence within the housing. This turbulence mixes the incoming synthetic and wood pulp fibers, which are then drawn by the vacuum onto the foraminous belt.

These two known web formers suffer several disadvantages. For example, the Dan Web and M & J Web Formers experience difficulty in producing a mat having a homogeneous blend of synthetic and wood pulp fibers. Furthermore, the Dan Web and M & J Web Formers are not known to enhance the Z tensile strength of the resulting mat. Additionally, the mats produced by these methods are very stiff and have extremely poor drape characteristics. These mats also have an uneven upper surface, resulting in a nonuniform mat thickness. Furthermore, the Dan Web and M & J Web Formers are not understood to vary the hydrophobicity of a mat thereby produced. Also, the Dan Web and M & J Formers have relatively slow mat production line speeds.

A variety of other methods of making limited life pads and other articles are discussed in U.S. Pat. No. 4,900,377 to Redford et al., which is hereby incorporated by reference as to the teachings therein.

Therefore, although other methods and devices have been used for blending cellulosic and synthetic fibers, and other articles have been produced using such methods and devices, a need exists for an improved method, apparatus and article which are directed toward overcoming, and not susceptible to, the above and other limitations and disadvantages.

SUMMARY OF THE INVENTION

It is an overall object of the present invention to provide an improved method and apparatus for blending and for air-laying cellulosic and synthetic fibers, and to provide an improved article which may be produced using the improved method and apparatus.

A further object of the present invention is to provide an improved method for the controlled on-line blending and air-laying of cellulosic and synthetic fibers, and for subsequently thermobonding such air-layed fibers.

An additional object of the present invention is to provide an improved metering system for synthetic fibers for use in providing a homogeneous blend of the synthetic fibers and cellulosic fibers.

A further object of the present invention is to provide an improved metering system for metering and blending synthetic fibers of widely varying lengths, such as ranging in length from about one millimeter (1 mm) to about 25 mm with cellulosic fibers.

Another object of the present invention is to provide an improved metering system for metering a desired amount of synthetic fibers and blending the metered amount of synthetic fibers with cellulosic fibers in any desired blend ratio.

Still another object of the present invention is to provide an improved metering system for simultaneously feeding synthetic fibers having several different lengths, deniers or SAP, for subsequent blending with cellulosic fibers.

Yet another object of the present invention is to provide an improved method of blending synthetic and cellulosic fibers which may be controlled so as to create a hydrophobic mat of material or a hydrophilic mat of material from synthetic fibers which have a normally hydrophobic fiber finish.

A further object of the present invention is to provide an improved blended mat with a basis weight ranging at a low end to fifty or less grams per square meter using standard hammermill vacuum forming equipment.

An additional object of the present invention is to provide a homogeneously blended mat of synthetic and cellulosic fibers having a very high uniformity in such characteristics as basis weight, strength and dispersion of fibers in the blend.

An additional object of the present invention is to provide a blend of synthetic and cellulosic fibers which may be controlled so as to provide an article having an enhanced high X–Y tensile strength.

An additional object of the present invention is to provide a blend of synthetic and cellulosic fibers which may be controlled so as to provide an article having an enhanced high Z tensile strength.

Another object of the present invention is to provide an improved method of controlled blending of synthetic and cellulosic fibers which creates a very soft mat with very high levels of drape both before and after bonding.

Still another object of the present invention is to provide a mat of synthetic and cellulosic fibers, with the mat having very high levels of drape before and especially after bonding.

Yet another object of the present invention is to provide an improved mat of a blend of synthetic and cellulosic fibers which is launderable.

A further object of the present invention is to provide an improved bonded mat having a core comprising a bonded homogenous blend of synthetic and cellulosic fibers sandwiched between facing and backing sheets.

According to one aspect of the present invention, a method is provided of forming a mat of cellulosic and synthetic fibers including the step of blending cellulosic fibers with a metered amount of synthetic fibers to form a fiber blend. In a screening step, the fiber blend is screened through a screen having apertures of a selected aperture size to provide a screened blend. In a depositing step, the screened blend is deposited as a mat on a mat-forming device to provide a mat of blended cellulosic and synthetic fibers.

According to another aspect of the present invention, a method of combining cellulosic and synthetic fibers to form a mat includes the step of fiberizing a sheet of cellulosic material into cellulosic fibers. In metering and injecting steps, a desired amount of synthetic fibers is volumetrically metered and injected into the cellulosic fibers. In a blending step, the cellulosic fibers and the synthetic fibers are blended to form a fiber blend. In an dispersing step, the fiber blend is dispersed through a fiber disperser having apertures to provide a dispersed blend. In a collecting step, the dispersed blend is collected as a mat on a fiber collector to provide a mat of blended cellulosic and synthetic fibers.

In an illustrated embodiment, in the metering step, the synthetic fibers are metered using a volumetric type feeder. In a bonding step after the collecting step, the mat is bonded, such as by using a thermobonder. In a preliminary fiber disperser selection or choosing step, the fiber disperser aperture size is chosen so as to vary the desired mat characteristics. The fiber disperser may be a screen having a plurality of apertures therethrough. For example, by appropriate selection of the aperture size, it has been discovered that the tensile strength of the resulting mat may be varied from a high Z tensile strength to a high X–Y tensile strength. In this description, X–Y tensile strength refers to the strength in the plane of the sheet or mat while Z tensile strength refers to the strength in a direction normal to the plane of the sheet. By selecting the aperture size and shape in accordance with the invention, the water absorbency characteristics of a mat formed using a synthetic fiber having a normally hydrophobic finish may be varied from hydrophobic to hydrophilic, that is, from repelling water to absorbing water. Additionally, the aperture size may be chosen to provide a mat which is launderable and has an increased uniformity of blend, as well as excellent drape characteristics.

According to an additional aspect of the present invention, a bonded mat is provided having desired mat characteristics. The bonded mat comprises a dispersed fiber blend of cellulosic fibers blended with a volumetrically metered amount of synthetic fibers. Other fibers may also be included in the core forming mixture, such as other nonthermoplastic synthetic fibers and natural staple fibers, such as rayon, cotton and the like. The fiber blend has been dispersed through a fiber disperser with apertures of a preselected aperture size, deposited on a mat-forming device, and bonded. Although adhesive and other bonding techniques may be used, preferably the mat is thermobonded.

In an illustrated embodiment, the mat may be sandwiched between a facing sheet and a backing sheet. Prior to being bonded, the screened fiber blend may be deposited upon a facing sheet of a nonwoven air permeable material. Also prior to bonding, a backing sheet of a nonwoven air permeable material may be placed over the mat to sandwich the mat between the facing and backing sheets. Alternatively, after bonding, a backing sheet of a liquid impermeable material may be placed over and secured to the bonded mat or core to sandwich the core between the facing and backing sheets.

According to yet another aspect of the present invention, a fiber blending apparatus is provided for blending cellulosic and synthetic fibers to form a mat. The fiber blending apparatus includes a volumetric type feeder of a type which receives incoming bulk synthetic fibers, typically in fluff form, and meters the received fibers. The feeder provides a metered amount of synthetic fibers which leave the feeder at a desired rate. The fiber blending apparatus also includes a fiberizer such as a hammermill, disk refiner, fluffer or other mechanical fiberizer apparatus with a fiberizing blending chamber. The blending chamber receives the metered amount of synthetic fibers from the feeder at the desired rate along with cellulosic fibers. The fiberizer blends the received fibers within the blending chamber. The fiberizer may also have an air-laying chamber which communicates with the blending chamber through an apertured fiber disperser, such as a screen, having a plurality of apertures therethrough of a predetermined or preselected aperture size. Within the air-laying chamber the fiberizer may have a fiber collector, such as a foraminous endless belt. A vacuum may be drawn across the fiber disperser to aid in extracting the blended fibers from the blending chamber through the disperser. In the case where a foraminous belt is used, the vacuum may be drawn across the belt and disperser to assist in depositing and holding the extracted fibers on the foraminous belt to form the mat. The disperser may have apertures sized and shaped to impart a desired contour to fibers passing therethrough for use in controlling the characteristics of a mat made from such fibers.

In an illustrated embodiment, the apparatus may also include a fiber opening system for opening and fluffing synthetic fibers, such as provided in bale form, a bonder, such as a thermobonder, a facing sheet handling system, and a backing sheet handling system (if facing and backing sheets are used). The air-laying chamber may also include a scalper roller for removing undesirable fiber masses from an upper surface of a collected mat. The apparatus may also include an optional feedback path for feeding back the removed undesirable fiber masses to the blending chamber for refiberization. The air-laying chamber may also include means for receiving and blending a third type of fiber with the dispersed cellulosic and synthetic fiber blend.

The present invention relates to the above features and objects individually as well as collectively. These and other objects, features and advantages of the present invention will become apparent to those skilled in the art from the following description and drawings.

BRIEF DESCRIPTION OF THE DRAWINGS

FIG. 1 is a schematic side elevational view of one form of an apparatus of the present invention for carrying out one form of a method of the present invention;

FIG. 2 is a perspective view of one form of an article comprising a towel in accordance with the present invention;

FIG. 3 is a schematic side elevational view of one form of a portion of a fiberizer shown in FIG. 1; and FIG. 4 is a schematic front elevational view of the fiberizer portion of FIG. 3.

DETAILED DESCRIPTION OF A PREFERRED EMBODIMENT

FIG. 1 illustrates an embodiment of a fiber blending system or apparatus 10 constructed in accordance with the present invention for the on-line blending and air-laying of fibers to form articles, such as a towel 12 shown in FIG. 2, having various desired characteristics. The fiber blending system 10 illustrates one manner of practicing a method of forming an article such as towel 12 in accordance with the present invention. The towel 12 may include a bonded core 14 of a fiber blend which may be formed as described below. The core 14 is sandwiched between an optional facing layer or sheet 16 and an optional backing layer or sheet 18, with sheets 16 and 18 of a cover stock material described further below.

Synthetic fibers 20 used to form core 14 may be supplied formed in a bale 21 to a fiber opening system 22, such as a conventional insulation blower opening system. The opening system 22 receives, opens and fluffs the synthetic fibers 20 from the bale 21 to provide fluffy bulk synthetic fibers.

The synthetic fiber bale 21 may be comprised of commercially available thermoplastic fibers which are typically made from thermoplastic polymers. These thermoplastic fibers have a high surface area to diameter ratio and are capable of melting when subjected to heat. Representative thermoplastic fibers are made from polyethylene, polypropylene, copolymers of ethylene and propylene, and copolymers of propylene and other 1-olefins, such as 1-butene, 4-methyl-pentene-1, and 1-hexene. Grafted polyolefins pulps may also be used, in which maleic anhydride or styrene groups are grafted. In some embodiments, the thermoplastic fibers are composed embodiments, being composed of mixtures of two or more types of thermoplastic fibers. Bicomponent fibers, such as comprised of polyethylene and polypropylene or other materials, may also be used. Fibers coated with a thermoplastic material are yet another example of a suitable fiber. Polyester fibers are still another example of suitable synthetic fibers. Cellulose acetate is a further example of a suitable fiber. The synthetic fibers 20 may be coated with various compounds to enhance or alter their performance, both in the mat forming process and in the finished product. Suitable commercially available products for making the thermoplastic fibers include PLEXAFIL™ from E. I. dupont de Nemours, a polyethylene based product; KODEL® 410 from Eastman Kodak Corporation, a polyester based product; and Vinyon® from Hoechst-Celanese Corporation.

After the synthetic fiber bale 21 has been opened and separated by the fiber opening system 22, the now fluffy mix of synthetic fibers 20 exit system 22 through a conduit 24. A transfer fan 26 may be used to assist in delivering the bulk synthetic fibers 20 through conduit 24 and a conduit 28 to an inlet of a volumetric type feeder 30.

The illustrated volumetric type feeder 30 includes an inclined foraminous endless conveyer belt 32 with an upper surface propelled upwardly by motor means (not shown) to ascend the incline. Preferably, by adjusting the motor means, the speed of the belt 32 may be varied to vary a rate at which the fibers 20 leave the feeder 30. The incline provides the belt 32 with a lower end 34 and an upper end 36. The incoming fluffy bulk synthetic fibers 20 are propelled from conduit 28 under the force provided by the transfer fan 26 to land toward the belt lower end 34. The feeder 30 includes vacuum means, such as a feeder vacuum provided by a feeder vacuum fan 38, which draws the feeder vacuum through a conduit 39. This vacuum draws air downwardly through the foraminous belt 32 to draw the bulk synthetic fibers received from conduit 24 onto the upper surface of the belt 32. Preferably, this vacuum may be varied by adjusting dampers (not shown) or by varying the speed of fan 38, to vary the density of the fibers 20 drawn onto the belt 32.

One or more scarfing rolls, spinner bars, doctor rolls or scalping rollers, such as rolls 40 and 42, are located a distance above the upper surface of belt 32 near the upper end 36. The scalping rolls 40, 42 typically have a shaft with needles or teeth projecting outwardly from the shaft. These teeth comb the top surface of the bulk fibers traveling along the upper surface of belt 32. The forced entry provided by fan 26 of fibers 20 above the belt upper end 36 cleans the top of the scalping rollers 40 and 42. Excess fibers removed by the scalping rollers may travel over the top surface of rollers 40, 42. These excess fibers are blown from the rollers downwardly toward the belt lower end 34 for deposit there with the incoming fibers. Preferably, the distance between the scalping rollers 40, 42 and the upper surface of belt 32 is variable to thereby vary the volume of fibers between the rollers 40, 42 and the upper surface of belt 32 and leaving the feeder 30.

The feeder 30 serves to meter and measure the amount of fibers 20 leaving the feeder on a volumetric basis. In the preferred embodiment, the amount of synthetic fibers 20 leaving the feeder may be variably adjusted by coordinating the feeder vacuum, the scalping roller distance and the belt speed. For example, the amount of fibers exiting the feeder 30 may be increased by increasing the feeder vacuum to provide a denser mat of synthetic fiber adhering to the belt 32, and the vacuum may be decreased to decrease the mat density. By raising the height of the scalper rollers 40, 42 relative to belt 32, the volume of the mat may be increased, whereas by lowering the rollers 40, 42 the volume may be decreased. Additionally, the amount of fibers exiting from the feeder 30 may be determined by the speed of belt 32.

In a preferred manner of controlling the feeder 30, the feeder vacuum supplied by fan 38 is set at a fixed value, and the height of the scalping rollers 40, 42 is also set at a fixed distance. With these two variables fixed, the amount of fibers exiting the feeder 30 may be varied by varying the speed of belt 32. In this manner, a metered amount of synthetic fibers are provided by the feeder 30. Such a feeder 30 may be constructed using a volumetric type feeder supplied by the Osprey Corporation of Atlanta, Ga., with minor modifications made to the feeder. This feeder is modified such that the belt 32 is substantially supported and leveled on an upward incline, conventional scalping rollers 40 and 42 for handling bulk synthetic fibers are selected, air flow is directed and balanced within the chamber 43 to enhance mat formation uniformity and feeding, and optical sensing eyes (not shown) within the feeder monitor the synthetic fibers within the feeder 30.

The metered quantity of synthetic fibers 20 is lifted from the upper end 36 of belt 32 by an aerating roller 44. The aerating roller 44 picks and lifts the metered synthetic fibers off of belt 32 and aerates the fibers. The aerated metered fibers travel through conduit 46 to a primary blower 48. The primary blower 48 delivers the metered synthetic fiber through conduit 49 to a fiberizer 50, such as, a hammermill, disk refiner, fluffer or other mechanical fiberizer apparatus.

The fiberizer 50 has a fiberizing blending chamber 52 which receives the metered synthetic fibers 20 from conduit 49. The fiberizer is illustrated as a hammermill 50 including a rotary hammer 54 which rotates within chamber 52. One or more rolls 56, 58 of sheets of cellulosic fibers 60 are fed into the blending chamber 52 where they are fiberized. During fiberization, the rotary hammer 54 breaks the cellulosic sheets into fiber form. The cellulosic fiber sheets are fed into the blending chamber 52 at a substantially constant amount and rate.

The cellulosic fibers 60 may be wood pulp fibers obtained from well known chemical processes such as the kraft and sulfite processes. In these processes, the best starting material is prepared from long-fiber, coniferous wood species, such as pine, douglas fir, spruce and hemlock. Wood pulp fibers can also be obtained from mechanical processes, such as ground wood, refiner mechanical, thermomechanical, chemimechanical, and chemithermomechanical pulp processes. Recycled or secondary wood pulp fibers and bleached and unbleached wood pulp fibers can be used. Details of the production of wood pulp fibers are well known to those skilled in the art. These fibers are commercially available from a number of companies, including Weyerhaeuser Company, the assignee of the present application.

Also, depending on the particular application, other absorbent materials may be added to the mixture, such as desiccants, superabsorbent materials, and any other absorbent or adsorptive material. Representative examples include activated carbon, acid clay, active alumina, diatomaceous earth, silica gels and the like. Relatively newly developed superabsorbent polymers, such as a cross-linked polyacrylate, commercially available under the brand name "Drytech" from the Drytech Chemical Company, may also be included. Other absorbent substances generally used in the form of a powder can conveniently be fixed in the core 14 in accordance with the process of the present invention.

In addition, oil absorbent materials such as polymers, including polynorbornene available under the brand name "Norsorex" from C.d.F. Chemie of France, may be included. In addition, odor absorbing or deodorizing materials such as baking soda, cedar oil, and other fragrances may be included in the core forming mixture. Eventual thermobonding of the core discussed further below helps fix these materials in place. Alternatively, instead of including these absorbent materials in the core forming mixture prior to bonding, they may be placed on one or both surfaces of the core 14 after thermobonding. These materials may be included in an adhesive coating on the core 14 or simply sprayed on the core in liquid form and allowed to dry.

The metered amount of synthetic fibers 20 and the cellulosic fibers 60, as well as any other desired additives as discussed above, are blended into a homogeneous mixture by the action of the rotary hammer 54 in chamber 52. This simultaneous fiberization of the sheet of pulp and the blending of the cellulosic fibers 60 with the synthetic fibers 20 advantageously saves energy, initial equipment costs, and plant floor space, by not requiring separate units to accomplish the fiberization and blending steps.

The homogeneous blend of fibers is extracted from the blending chamber through an apertured fiber disperser, such as a screen 62, having a plurality of preselected apertures 64 therethrough. A variety of varying apertures sizes and shapes may be used. For example, the apertures may be circular, oval, square, rectangular, or trapezoidal. For synthetic fibers having a nominal ½ inch length, and cellulosic fibers 5 mm or less in length, the aperture size may be selected between ⅛ inch and one inch. Several examples are set forth below using these fiber sizes and a screen having screen apertures preselected to be ¼ inch in diameter and ⅜ inch in diameter, referred as a ¼ inch screen and as a ⅜ inch screen, respectively. However, other mats have been made using the ¼ and the ⅜ inch screens and fibers up to one inch in length.

In a preferred embodiment, the apertures 64 are of a uniform size, and evenly spaced about the screen 62. Preferably, each aperture has one dimension which is less than the length of the synthetic fibers. Of course, larger apertures may be selected to provide a more laminar mat. Smaller apertures tend to increase the residual time of the fibers within the blending chamber 52, during which time the fibers are subjected to more rolling and pilling action by the hammer 54 to impart a desired contour to the fibers which eventually pass through the screen 62.

The homogeneous blend of fibers passes through the screen 62 into an air-laying chamber 66 defined by a shroud 68. The screened blend of fibers within chamber 66 are deposited or collected on a fiber collector, such as on an upper surface of a foraminous endless conveyor belt 70. Typical line speeds for the belt would range from 100 to 500 feet per minute or greater, with 350 feet per minute being expected as a normal operating speed. To aid in extracting the blended fibers from chamber 52 through screen 62, the forcing action of blower 48 is vacuum assisted. The air from chambers 52 and 66 is drawn through screen 62 and the foraminous belt 70 into conduit 72 by a main vacuum fan 74. The density of the mat 90 deposited on belt 70 may be varied by varying the vacuum applied by fan 74 in the same manner as described above for varying the feeder vacuum.

The feeder vacuum fan 38 and the main vacuum fan 74 deliver the vacuum air received from the respective volumetric type feeder 30 and hammermill 50 through respective conduits 76 and 78 to a filter box or dust collector 80. The dust collector 80 may include various dust collecting devices, such as filter elements such as 82 which filter and clean the air received by collector 80 prior to venting the air 84 to atmosphere. The dust collector 80 removes the fine fiber particles which passed through belts 32 and 70 and entraps these fine fiber particles therein so only clean air 84 is released to the atmosphere. Thus, both the volumetric type feeder 30 and hammermill 50 are negative pressure systems, which advantageously inhibits loose fibers from escaping from the fiber blending apparatus 10.

The forcing action of blower 48 and the vacuum provided by the main vacuum fan 74 also aid in directing the screened fibers through chamber 66 for deposit onto belt 70. Included within the hammermill shroud 68 are two scalping rollers, spinner rollers, scarfing rollers or doctor rolls 86, 88. The rollers 86, 88 each have a shaft with a plurality of needles or teeth projecting outwardly therefrom. The teeth of rollers 86, 88 comb an upper surface of a screened blended fiber mat 90 deposited on belt 70 to remove undesirable fiber masses from the mat upper surface. Upon exiting shroud 68, the blended fiber mat 90 passes through a debulker, such as a debulking roller 92, which compress the mat 90.

Thus, a homogeneous blended fiber mat 90 is provided which does not stratify. Stratification occurs when the synthetic fibers 20 settle out and separate from the wood pulp fibers 60. Stratification would inhibit the uniformity of characteristics in the resulting mat such as the uniform thermobonding of mat 90 in the event the mat is thermobonded. For example, in other known systems due to the aerodynamic characteristics of the fibers, the heavier wood pulp fibers 60 drop more quickly than the lighter weight synthetic fibers 20 which causes stratification. However, if in a given application such stratification is desired, it could easily be accomplished using the fiber blending system 10. For example, if only wood pulp fibers are desired in a particular layer, the flow of synthetic fibers 20 may be momentarily interrupted, such as by activating a shut off valve (not shown) inserted in conduit 48.

In the illustrated embodiment, the hammermill 50 includes a facing sheet handling system comprising cover stock supply rolls 94 and 96 of facing sheet material. The rolls 94 and 96 may be alternatively selected to supply the facing sheet 16 (FIG. 2). The facing sheet material from rolls 94, 96 passes through an edge tracking guide train 98 which evens the edges of the sheet with the edges of belt 70. The facing layer 16 typically comprises a pre-formed sheet or web of material which may be of a nonwoven thermoplastic containing material being perforated or otherwise breathable to be air permeable. To prevent the facing sheet 16 from melting, if thermobonded (discussed further below), the facing sheet would be selected in this case to a have a higher melting point than the melting point of the synthetic fibers which are to be melted during thermobonding.

Thus, the selection of the facing sheet material will depend at least in part upon the thermoplastic fibers included in the core. Representative facing sheet materials include thermoplastic coated materials such as rayon which is resin or otherwise coated with a thermoplastic layer, polyolefin materials, spun laced polyester and spun bonded polyester and polypropylene, thermobonded polyester and polypropylene, carded polyester and polypropylene, melt blown polypropylene, polyethylene films of varying densities, polypropylene films, apertured films and other suitable materials apparent to those skilled in the arts. Some commercially available suitable nonwoven filament products include Cerex®, a nylon material from Fiberweb N. A.; Reemay®, a spun bonded polyester material from Intertec Corporation; and Sontara®, a spun laced polyester product from DuPont Corporation.

Again, a wide variety of facing sheet materials may be used. These facing sheets may be of a thermoplastic or thermoplastic containing material for those applications in which the facing sheet is to be thermobonded to the core. Facing sheets of spunlaced or resin bonded rayon, acrylic, and cotton blends, including those with acrylics, may also be thermobonded to the core. Facing sheets of these or of other materials may be secured to the core in other manners, such as by an adhesive. Nonwoven materials are exemplary facing sheets because such materials readily allow the passage of liquids to an absorbent core.

In the illustrated embodiment, the blended fiber mat 90 is deposited over the facing sheet 16, and the mat 90 and optional facing sheet 16 exit hammermill 50. After exiting, the mat 90 and facing sheet 16 may optionally be thermobonded by thermobonder 100 shown in dashed lines. A conveyer comprising an foraminous endless belt 102 transports the mat 90 and facing sheet 16 from the hammermill 50 through thermobonder 100. Upon passing through thermobonder 100, the blended fiber mat 90 is bonded to form a bonded mat or core 14 such as may be used in towel 12 (see FIG. 2). Alternatively, thermobonding may be done at some later point in time, and the mat 90 and facing sheet 16 may be gathered for storage and further processing as roll 104. As yet another option, the core may be adhesively bonded with or without cover sheets. Alternatively, the roll 104 may be replaced with further article processing equipment (not shown), such as an embossing device, a cutting mechanism for separating the towels 12, a stacker, a storage bin, or a packaging apparatus.

If thermobonder 100 is employed as shown, the thermobonder heats the fiber mat 90 to a temperature above the melting point of at least one synthetic fiber material therein. For example, the melting point of some types of polyethylene fiber is 122° to 134° C. while the melting point of some types of polypropylene fiber is 160° to 165° C. Heating the such a mat 90 to a temperature of 140° C. heat fuses the mat 90 to form the core 14. Although calendars, infrared heaters, and other heating devices may be employed to heat fuse the core, the illustrated thermobonder 100 comprises a flow-through dryer. The exact heating conditions, which can be readily ascertained by one skilled in the art, must be determined for the specific fiber blend being used. The time that the core spends within the thermobonder 100 is also readily ascertainable by one skilled in the art. Generally this time ranges from about one hundred milliseconds to one minute depending in part upon the temperature of the thermobonder and the line speed at which the belt 102 is traveling. The thermobonded mat comprising core 14 may be gathered for storage and processing on roll 104, or subsequent handling systems may be employed.

In the illustrated embodiment, the fiber blending apparatus 10 includes a backing sheet handling system located downstream of the hammermill 50. The location of the backing sheet handling system depends upon the type of backing sheet material selected. If the cover stock of backing sheet 18 (FIG. 2) is of a material which is perforated or otherwise air permeable like facing sheet 16 described above, the backing sheet handling system may be located either upstream or downstream of the thermobonder 100. For example, a backing sheet 18' of air permeable material may be supplied from roll 106 and may be applied to overlay the exposed blended fiber mat 90 using roller 108 located between the hammermill 50 and thermobonder 100. The air permeable backing sheet 18' allows the heated gas of the thermobonder 100 to pass therethrough and bond the mat 90 to form the bonded core 14. The backing sheet 18' may be attached to the core and facing sheet 16 by adhesive or other means, or by using the thermobonder 100 to bond the backing sheet 18' to the core 14. In this manner, the fiber core is sandwiched between facing and backing sheets 16 and 18'.

If the backing sheet 18" (see FIG. 2) is of a plastic or poly material which is moisture, liquid or air impermeable, it is typically applied after the mat 90 has passed through the forced air thermobonder 100. For example, a backing sheet 18" of air impermeable material may be supplied from roll 110 and may be applied to overlay the exposed bonded fiber mat 90 or core 14 using roller 112 located downstream from the thermobonder 100. In this case, the air impermeable backing sheet 18" does not inhibit the flow of heated gas through the mat 90 in the thermobonder 100. The backing sheet 18" may be then attached to the core and facing sheet 16 by adhesive or other means. In this manner, the fiber core is sandwiched between facing and backing sheets 16 and 18". If the backing sheet 18 is applied either before or after thermobonder 100 it may also be rolled onto roll 104 with the core and optional facing sheet 16 for storage or later processing.

Thus, the backing sheet 18 may be identical to the facing sheet 16 and may be secured to the core 14 during thermobonding. However, the backing sheet may also be comprised of a film having a melting point which is below the melting point of the thermoplastic fibers of the core which are melted during heat fusing of the core. In such a case, these materials may be secured to the core 14 following the thermobonding step, such as being supplied from a supply roll 110 and adhered by a calendar and roller 112. If the backing sheet 18 comprises a liquid impermeable material it assists in containing liquids absorbed by the core 14 and through the facing sheet 16. Suitable backing sheet materials include, in addition to those mentioned above in connection with the facing sheets, films of polyethylene, polypropylene and polyester and blends of these materials, linear low density polyethylene films, nylon, polyvinylchloride films and fire retardant films. An example of a commercially available suitable film is Saran® from Dow Chemical Corporation.

Also, the backing sheet materials may comprise thermoplastic materials so as to permit thermobonding or thermosetting of the backing sheet along an eventual peripheral edge margin 120 and at field bond areas or points 122 of the article 12 (FIG. 2). Alternatively, the towel 12 may be densified along peripheral edge 120 and densified at field bond points 122. The manner of densifying peripheral edge 120 and field bond points 122 may be as set forth in the Redford et al. U.S. Pat. No. 4,900,377 incorporated by reference hereinabove. The densified edge 120 serves to entrap moisture within the core 14 if of a hydrophilic construction. The field point bonds such as 122 provide additional structural integrity during use, and may be arranged to enhance the aesthetic appearance towel 12.

Referring now to FIGS. 3 and 4, a preferred embodiment for a portion of the hammermill fiberizer 50 is shown. The apparatus 10 may also include a feedback path for feeding back removed undesirable fiber masses from scalper rollers 86, 88 to the blending chamber 52 for refiberization. In the illustrated embodiment, the shroud 68 includes gathering means, such as a vacuum pickup chamber 130 located over the scalping rollers 86 and 88. With a fiber blend formed of synthetic fibers 20 which are longer than the wood pulp fibers 60, the scalping rollers 86, 88 tend to pick up the longer synthetic fibers more than the shorter wood pulp fibers. The teeth of rollers 86, 88 also remove other undesirable fiber masses and chunks deposited along the mat upper surface. To clean the teeth on the scalping rollers 86, 88 these longer synthetic fibers are gathered and extracted by the vacuum pickup 130. The gathered undesirable fiber masses are then removed from the system or more preferably fed back to the blending chamber 52 through a feed back path comprising conduit 132, blower 134 and conduit 136. This gathering and feeding back of the excess synthetic fibers reduces the concentration of synthetic fibers on the surface in the final product. The removal of the undesirable fiber masses aids in providing a more uniform mat 90.

The air-laying chamber 66 may also include means for receiving and blending a third type of fiber comprising tertiary fibers 138 with the dispersed cellulosic and synthetic fiber blend. The tertiary fibers 138 may be injected into the air-laying chamber through an aperture 140 in shroud 68. The injection of tertiary fibers 138 may be used to vary the characteristics of mat 90, as well as the resulting core 14. For example, the tertiary fibers 138 may be longer than those fibers of the screened fiber blend exiting the screen 62. Longer tertiary fibers 138 tend to land substantially parallel to the upper surface of belt 70 and have the effect of increasing the X-Y tensile strength of the resulting mat 90. For example, using tertiary fibers 138 of a high melt polyester having a nominal length of ¾" inch, the X-Y tensile strength of the resulting mat may be substantially doubled. It is apparent that other types and lengths of tertiary fibers 138 may be used to vary the mat characteristics.

Referring to FIG. 4, additional turbulence may be introduced into the air-laying chamber to enhance the mixing of the screened fiber blend exiting screen 62, as well as to enhance the mixing of any tertiary fibers 138 with the screened fiber blend. In one approach for providing this additional turbulence, compressed air 150 is supplied through conduits 152, 154 to opposing or transversely spaced sides the shroud 68. Nozzles 156 and 158 receive the air 150 from the respective conduits 152 and 154. The nozzles 156, 158 create turbulence 160 within the air-laying chamber to assist in the mixing and blending of these screened fibers and any tertiary fibers 138.

After bonding, the bonded mat 90 or core 14 has desired characteristics which may be varied by varying a variety of factors. For example, the type, as well as the metered amount, of synthetic fibers 20 fed to the hammermill 50 may be varied. Also, the concentration or ratio of cellulosic fibers 60 to synthetic fibers 20 may be varied. The density of the mat 90 deposited on belt 70 may also be varied, such as by varying the vacuum applied by the main vacuum fan 74. The thickness and compactness of the mat 90 exiting the hammermill 50 may be varied by adjusting the position of the scalper rolls 86, 88 relative to the conveyor 70 and the position of the debulker roll 92. Also, the thermobonding time and temperature may be varied by adjusting the thermobonder heating elements and air flow, and the speed of belt 102. It is apparent that the characteristics of the mat 90 prior to bonding may also be varied in the same manner.

Additionally, in accordance with the present invention, the choice of fiber length, and the selection of the configuration and size for the screen apertures 64, that is, the screen size selection, has a significant and unexpected effect on the properties of mat 90, both before and after thermobonding. While the illustrated samples discussed below used apertures 64 having a circular aperture, other aperture shapes may also be used. For example, a ¼ inch square aperture, or a trapezoidal aperture having a ¼ inch height, may be used with ½ inch long synthetic fibers to produce a mat having enhanced strength in the Z direction. An oval aperture substantially ¼ inch by ⅜ inch may produce a mat having a compromise between the X–Y tensile strength and Z tensile strength enhancements provided by circular apertures of ⅜ and ¼ inch, respectively. An oval aperture is expected to produce a mat having some pills and balls of fibers, and having laminar oriented fibers which are substantially parallel to the upper surface of conveyer 70. Other aperture configurations may also be used. Thus, the fiber blending apparatus 10 may be used to practice the method of the present invention to provide articles, such as towel 12, having various desired mat characteristics.

Several sample towels 12, designated sample towels A, B and C, were manufactured according to the present invention by varying the type of synthetic fiber 20 used and the size of screen 62. In connection with these samples, the various characteristics and properties of the thermobonded cores and of the composite articles were measured by the methods listed in Table I. In this table, ASTM refers to the American Society of Testing Materials, TAPPI refers to the Technical Association of Pulp and Paper Industry, and INDA refers to the Association of Nonwoven Fabrics Industry. Also in Table I, WEYCO refers to test methods of the Weyerhaeuser Company, the assignee of the present application.

The Weyerhaeuser migration test, WEYCO Test Method No. 88-50-1, tests the average migration area of a solution through a specimen. A solution of instant coffee and deionized water is mixed. Enough coffee is added until it is difficult to dissolve, making the water very dark in color. Ten milliliters of the coffee solution are poured onto the center of a specimen, and a timer is started. After two minutes, the length and width of the dark stain are marked with a pen. Any wavering in the margin of the liquid stain are averaged during this marking. The marked length and width are then measured in centimeters (cm) and a migration area is calculated by multiplying the measured length by the measured width. Thus, the migration is reported as an average migration area in units of $cm^2$.

The Weyerhaeuser wetability test, WEYCO Test Method No. 90-02-1A, evaluates the ability of a material to absorb various liquids. A test specimen of material is layed flat on a smooth and nonabsorbing flat test surface which is preferably made of plastic or glass. A 9 mm thick metal ring, having a 16 mm inner diameter hole is placed in the center of the specimen to rest at least 5 cm from the edges of the specimen. Then 2 cc of a test liquid, such as deionized water, are measured into a plastic syringe. Using the syringe, the liquid is smoothly squirted into the center of the ring, and simultaneously a timer is started. The timer is stopped when no freestanding liquid remains on the specimen. Five specimens are thusly tested, and the results averaged and reported in seconds.

The Weyerhaeuser wipe dry test, WEYCO Test Method No. 90-41-1, quantifies the amount of liquid picked up by a specimen using a standard wiping method. A sled having a specimen taped thereto is drawn horizontally at a constant rate over a horizontal aluminum table having a puddle of deionized water spilled thereon. The horizontal table is mounted to a constant rate of elongation (CRE) type tester, such as that sold under the trade name "Instron." The aluminum table has a surface area of 20.25 inches by 6 inches, with a low friction pulley attached to one of the six inch wide ends. The test sled is a 63.5 mm square metal block which is approximately 6 mm thick, and wrapped with sponge rubber. The sponge rubber is flexible, smooth-faced and has a density of 0.25 $g/cm^3$. The total weight of the test sled is 200.0±0.5 grams. A test specimen of the towel sample is cut 3.0 inches in the cross direction, and 3.5 inches in the machine direction. The specimen is weighed to determine its initial weight. The specimen is adhered to the sled by taping the leading edge of the specimen to the leading edge of the sled, with the specimens adhered so that the pull direction is the same as the machine direction. The sled is then placed on the table at a maximum distance away from the pulley. Ten milliliters of deionized water are poured on the table surface directly in front of the sled. The sled is pulled by the CRE tester with a cable through a pulley, which translates the vertical travel of the CRE tester into horizontal sled motion across the table. The CRE tester draws the sled a distance of 12.67 inches at a rate of 50 inches per minute. The specimen is then removed from the sled and weighed to obtain a wet weight value. This test is repeated four times, and the results are averaged. Wipe dry is reported in percent, with wipe dry equalling the difference between the wet weight and the initial weight, with this difference then divided by the initial weight.

The Weyerhaeuser rewet test, WEYCO Test Method No. 86-24-2, is used to measure the amount of liquid that emerges from an absorbent core through a top sheet of the specimen to cause wetness on the outer surface of the specimen towel. A specimen of the sample towel, cut into a 10 cm square, is weighed dry and a testing filter paper is also weighed in the dry state. The specimen is then placed on a smooth, flat and nonabsorbent surface, preferably of a plastic or glass. A rewet apparatus is then placed square over the specimen. The rewet apparatus is a square block weighing 855 grams and having a hole extending substantially through the center of the test block. The hole has a multi-port orifice therein. Using a plastic syringe, deionized water in an amount equalling three times the weight of the specimen, is smoothly squirted into the center hole of the rewet apparatus. When all of the liquid has been absorbed into the specimen, a timer is started and the rewet apparatus removed. At the end of two minutes, the filter paper is placed on top of the specimen, and the rewet apparatus placed over both the specimen and filter paper. After one minute, the rewet apparatus is removed and the filter paper weighed. A rewet value is determined by subtracting the dry filter weight from the wet filter weight.

TABLE I

| | Property Measurements | |
|---|---|---|
| Characteristics | Test Methods | Units |
| Basis Weight | TAPPI T-410 OM | $g/m^2$ |
| Density | TAPPI T-410 OM | $g/cm^3$ |
| Bulk | TAPPI T-426 WD | $cm^3/g$ |
| Z Direction Tensile | TAPPI T-506 | $KN/m^2$ |

TABLE I-continued

Property Measurements

| Characteristics | Test Methods | Units |
|---|---|---|
| Strength | | |
| Liquid for Absorbent Capacity | ASTM-D 535 | ml/g |
| Migration | WEYCO 88-50-1 | cm² |
| Wetability | WEYCO 86-90-1 | sec. |
| Rewet | WEYCO 86-24-2 | grams |
| Handle-o-meter | INDA IST 90.0-75(R82) | grams |
| Wicking ("Absorption") | INDA IST 10.0-70-(R82) | sec. |
| Wipe Dry | WEYCO 90-41-1 | % |

Table II illustrates the test data for the samples A, B and C tested using the methods listed in Table I.

TABLE II

| SAMPLE | A | B | C |
|---|---|---|---|
| SCREEN SIZE, in. diam. | ¼ | ¼ | ⅜ |
| SYNTHETIC FIBERS KODEL ® | J-4686 | J-4589 | J-4589 |
| BASIS WT., g/m² | 208 | 212 | 205 |
| DENSITY, g/cm³ | .130 | .131 | .127 |
| BULK, cm³/g | | | |
| DRY | 7.71 | 7.64 | 7.89 |
| WET | 1.30 | 1.36 | 1.30 |
| DEMAND ABSORBENCY | | NOTE 1 | |
| INIT. RATE, ml/min | 9.40 | | 8.60 |
| ABSORB. RATE, ml/min | 0.65 | | 0.63 |
| DEMAND ABSORB, ml/g | 5.74 | | 4.72 |
| MIGRATION, cm² | 170 | NOTE 2 | 230 |
| Z TENSILE, KPa | | | |
| DRY | 34.2 | 30.1 | 21.9 |
| WET | 9.59 | 8.34 | 8.80 |
| WETABILITY, sec. | 6.50 | NOTE 2 | 7.71 |
| REWET, g | .554 | NOTE 2 | .455 |
| HANDLE-O-METER, g | | | |
| MD | 82.9 | 78.1 | 98.2 |
| CD | 31.9 | 27.8 | 42.8 |
| ALL | 56.2 | 52.0 | 68.4 |
| WICKING, sec. | | | |
| MD | 5.16 | >180 | 4.53 |
| CD | 7.38 | >180 | 5.69 |
| WIPE DRY, % | | | |
| TOP | 416 | 21.8 | 354 |
| BOTTOM | 460 | 23.9 | 334 |

NOTES:
1) sample would not draw water.
2) Water would not absorb into pad.
3) 23% Synthetic fibers, flat-pressed pads, and ¼" × ⅛" standard screen embossed.

The sample towels A, B and C each had facing and backing sheets 16, 18 of nonwoven Sontara® stock no. 8010, from the DuPont Corporation. The thermobonded core 14 was comprised of twenty-three percent synthetic fibers 20 with the balance being wood pulp fibers 60. Wood pulp fibers 60 and synthetic fibers 20 having a nominal ½ inch length were used in constructing these samples.

The synthetic fibers 20 used in sample towel A are from Eastman Chemical Products, Inc. (a subsidiary of Eastman Kodak Corporation) of Kingsport, Tennessee, and may be ordered as KODEL® stock no. J-4686. The KODEL J-4686 fibers have a hydrophilic fiber finish, which in combination with the ¼ inch screen size, are believed to be particularly advantageous in producing a sample A towel 12 having the desired characteristics set forth in Table II. The sample A towel is hydrophilic, and has excellent Z tensile strength and excellent drape characteristics, as evidenced by the low handle-o-meter "all" values. As mentioned in note 3 of Table II, the sample towels A, B and C were flat-pressed pads. By using an embossing roller in the manner set forth in U.S. Pat. No. 4,900,377 to Redford, et al., for example in the position of roller 112 in FIG. 1, the rotary embossed towels produced in this fashion have handle-o-meter "all" values of approximately 30. Therefore, the drape characteristics of embossed articles are substantially enhanced over that of the flat-pressed sample towels (see Note 3 in Table II).

The sample towels B and C each had a core 14 comprising synthetic fibers 20 which may be obtained from Eastman Chemical Products as KODEL® stock no. J-4589. The KODEL J-4589 synthetic fibers have a hydrophobic fiber finish. The sample C towel mat 90 was formed using a ⅜ inch size screen 62. The KODEL J-4589 hydrophobic finished fibers in combination with the ⅜ inch screen produced a hydrophilic towel C as expected, since the dominant proportion of the core comprises hydrophilic wood pulp fibers 60. The sample C towel had absorbencies just slightly lower than those of sample A which was produced using KODEL J-4686 hydrophilic fibers. Also, sample C has enhanced X–Y tensile strength, but is rather stiff, as evidenced by the high values of the handle-o-meter test.

The sample B towel was produced using the hydrophobic finished KODEL J-4589 fibers, nominally ½ inch in length, and a ¼ inch size screen 62. Surprisingly, the sample B towel is soft, hydrophobic, and has excellent drape characteristics that are actually better than the sample A and C towels. It was not expected that by merely changing the screen size (from ⅜ inch for sample C to ¼ inch for sample B), the hydrophilicity and hydrophobicity of the resulting towel would be so dramatically effected. Whereas the sample C towel absorbs water and sinks, the sample B towel floats on water (compare the demand absorbency, migration, strikethrough, and rewet test data shown in Table II). Furthermore, the wipe dry characteristic of sample B is extremely low as compared to the other samples. The sample B towel has a high Z tensile strength, just slightly less than the Z tensile strength of sample A, also formed using a ¼ inch size screen. The sample B towel is also very launderable, maintaining integrity during ten machine washings.

Although this invention is not limited by any theory of operation, a theory as to how the present invention is believed to provide the varying tensile strengths and other desirable characteristics by varying the screen size and synthetic fiber size and finish (hydrophobic or hydrophilic), will now be described.

Increased X–Y tensile strength is believed to be accomplished by passing longer fibers through the larger diameter screen openings, such as through the ⅜ inch screen. The longer fibers are deposited to lay substantially flat on belt 70, allowing the fibers to interweave with each other. The interweaved fibers enhance the X–Y tensile strength, because forces applied in the X–Y direction pull substantially along the inherently stronger length of the individual fibers.

Using the smaller ¼ inch size screen is believed to cause the fibers to bend in order to pass through the screen openings 64. It is believed that the fibers are "balled-up" or rolled by the rotary action of hammer 54 within blending chamber 52. The balled-up fibers form balls, nits or pills of fibers which are extracted through the screen 62. The fibers maintain the balled-up configuration as they are deposited on belt 70. The resulting mat 90 comprises a plurality of fiber balls or pills which have portions of the fibers extending upwardly in the Z direction. When the mat 90 is thermobonded by thermobonder 100, the resulting core 14 has some fibers which have been bonded in place to extend upwardly in the Z direction. The fiber strength is inherently greater along the length of a fiber which inhibits the core 14 from pulling apart in the Z direction. Thus, the upwardly extending fibers resist delamination of the core 14 in the Z direction. This property significantly enhances the launderability of the resulting towel 12. Also, the balled-up nature of the fibers is believed to enhance the drape characteristics, because the fibers are not all laying substantially flat in the X–Y direction with the individual fibers tending to resist bending, as demonstrated by the stiffness of sample C.

In operation, the fiber blending system 10 of the present invention receives a bale 21 of synthetic fibers 20 with a fiber opening system 22. The fiber opening system 22 separates, opens and fluffs the synthetic fibers 20 from bale 21. The fluffy bulk synthetic fibers are delivered from the fiber opening system 22 to a volumetric type feeder 30 via conduits 24 and 28 with the assistance of transfer fan 26. Under the force of the transfer fan, the bulk synthetic fibers 20 are delivered to a lower end 34 of belt 32. Any fibers along the top surface of the scalping rollers 40 and 42 are swept off the rollers and deposited with the incoming fibers at the belt lower end 34. A feeder vacuum is supplied by a feeder vacuum fan 38 via conduit 39 to draw the fibers 20 onto the upper surface of belt 32. The scalper rollers 40 and 42 determine the volume of fibers leaving feeder 30 at any given instant. The aerating roller 44 lifts the fibers from belt 32 for airborne delivery through conduits 46 and 49 to hammer mill 50, with the propulsion force being supplied by the primary blower 48.

The volumetric feeder 30 may be adjusted to supply a desired amount of synthetic fibers to the hammer mill 50 in a variety of ways. For example, the density of the fiber mat deposited on belt 30 may be varied by varying the feeder vacuum supplied by fan 38. The volume of fibers leaving the volumetric feeder may be adjusted by varying the distance of the scalping rollers 40 and 42 above the upper surface of belt 32. In a preferred embodiment, the scalping roller height or distance above belt 32 and the vacuum supplied by fan 30 are each set to a fixed constant value. Variations then in the amount of metered fibers leaving feeder 30 may be provided by adjusting the speed of belt 32, such as by increasing the belt speed to increase the amount of fibers supplied to hammer mill 50.

The hammer mill 50 receives the metered amount of synthetic fibers in the fiberizing blending chamber 52. The hammer mill 50 also receives cellulosic fibers such as wood pulp fibers 60 from supply rolls 56, 58. The rotary hammer mill 50 fiberizes and blends the synthetic fibers 20 and the wood pulp fibers 60 in the blending chamber 52. The operation of the hammer 54, blower 48 and main vacuum fan 74 cooperate to extract or draw the homogeneous blended fibers from chamber 52 into air-laying chamber 56 through the apertures 64 of screen 62.

The screened and blended homogeneous fibers are further mixed by introducing compressed air 150 through nozzles 156, 158 to the air-laying chambers 66. Through inlet 140, any tertiary fibers 138 may be added to the screened fiber blend and mixed therewith by the compressed air 150 emitted from nozzles 156, 158. The turbulated fiber mixture of synthetic, wood pulp and any tertiary fibers are then collected or deposited on the upper surface of foraminous belt 70 with the assistance of vacuum fan 74.

An optional facing sheet 16 of an air permeable material may be supplied from rolls 94 and 96 through guide train 98 onto belt 70, and the homogeneous blended fibers deposited as mat 90 thereon in the air-laying chamber 66. Scalping rolls 86 and 88 have teeth which comb the mat 90 prior to exiting shroud 68. The optional vacuum pickup 130 gathers any fibers from the teeth of the scalper rollers 86, 88 to provide a more uniform mat. The scalping rollers tend to remove undesirable fiber masses, such as longer synthetic fibers or larger chunks of fibers, which are gathered by the vacuum pickup 130. The gathered fiber masses are returned via the feedback path comprising conduit 132, blower 134 and conduit 136, to the blending chamber 52 for refiberization by the hammer 54. Beyond shroud 68, a debulking roller 92 compresses the mat before it exits the hammer mill 50.

The blended fiber mat 90 with optional facing sheet 16 may be taken up on roll 104 for subsequent storage or processing. Optionally, the fiber blending system may include a thermobonder 100 for thermobonding the mat 90 to form core 14 (see FIG. 2). An optional backing sheet 18 may be applied to overlay the exposed fiber mat 14 and sandwich the mat or core between the backing sheet 18 and facing sheet 16. If thermobonder 100 is used, a backing sheet 18' of an air impermeable material is applied from supply roll 110 using roller 112 located downstream of the thermobonder 100. This would be an equally suitable location for applying a backing sheet of an air permeable material. However, an air permeable backing sheet 18' may be supplied from roll 106 and applied over the mat 90 using roller 108, located between the hammer mill 50 and thermobonder 100. The reel 104 may be replaced by subsequent processing equipment (not shown), such as an embossing device (positioned at the location of roller 112), a cutting mechanism for separating the articles, such as towels 12, a stacker, a storage bin, or a packing apparatus.

In this manner, an article such as a bonded mat or towel 12 shown in FIG. 2 may be formed having desired mat characteristics, such as enhanced X–Y or Z tensile strength, or varying degrees of hydrophobicity or hydrophilicity, softness and drape. These characteristics may be varied by the selection and proportions of synthetic fibers 20 and cellulosic fibers 60, as well as by the selection of the size of screen 62, as well as varying other quantities, temperatures and times, such as by adjusting the volumetric feeder, the speed of belts 32, 70 and 102, and the temperature and air flow within the optional thermobonder 100. In the preferred embodiment, the towel 12 includes core 14 sandwiched between facing and backing sheets 16, 18. The towel 12 includes a densified peripheral edge 120, and a plurality of field point bonds 122 within the field of the towel defined by the densified edge 120.

In addition to wood pulp fibers 60 and synthetic fibers 20 mentioned above, other nonthermoplastic synthetic fibers and natural staple fibers, such as rayon, cotton, and the like may be included in the core forming mixture. Such other fibers may be introduced into the fiber blending system 10 with the synthetic fibers, with the wood pulp fibers, or separately as tertiary fibers 138 through the shroud inlet 140. Suitable tertiary fibers 138 which may used to increase the X–Y tensile strength of the resulting mat. The tertiary fibers 138 may be fibers having a melting point greater than the binding synthetic fibers. For example, suitable tertiary fibers 138 may be of a high melt polyester, nylon or rayon.

Having illustrated and described the principles of our invention with respect to a preferred embodiment, it should be apparent to those skilled in the art that our invention may be modified in arrangement and detail without departing from such principles. For example, other screen diameters and configurations may be used, as well as suitable material substitutions and dimensional variations for the screen apertures and fibers. Other combinations of aperture size, and fiber size, type and proportions may be implemented. We claim all such modifications falling within the scope and spirit of the following claims.

We claim:

1. A bonded mat produced by blending cellulosic fibers with a volumetrically metered amount of synthetic fibers, dispersing the blend through an apertured fiber dispenser onto a collector to form a mat comprising pills of balled-up cellulosic and synthetic fibers wherein portions of the fibers of the pills extend in an upward direction relative to the plane of the mat and thermobonding the mat.

2. A bonded mat according to claim 1 wherein the fiber blend was dispersed through a fiber disperser having an aperture size preselected to be substantially one-quarter inch in diameter so as to provide the bonded mat with the desired mat characteristic of enhanced Z tensile strength.

3. A bonded mat according to claim 1 wherein the fiber blend was dispersed through a fiber disperser having an aperture size preselected to be substantially three-eighths inch in diameter so as to provide the bonded mat with the desired mat characteristic of enhanced X–Y tensile strength.

4. A bonded mat according to claim 1 further including a facing sheet of a nonwoven air permeable material upon which the dispersed fiber blend was deposited prior to being thermobonded to provide a partially-covered bonded mat having an exposed fiber core.

5. A bonded mat according to claim 1 further including a backing sheet of a liquid impermeable material overlaying the exposed fiber core to thereby sandwich the core between the facing and backing sheets.

6. A bonded mat according to claim 1 further including a facing sheet and a backing sheet surrounding the bonded mat, with the facing and backing sheets each being of a nonwoven air permeable material.

7. A method of forming a mat of cellulosic fibers and synthetic fibers, comprising the steps of:

fiberizing cellulosic material into cellulosic fibers;

injecting synthetic fibers into the cellulosic fibers;

blending the cellulosic fibers with the synthetic fibers to form a fiber blend;

dispersing the fiber blend through a fiber disperser having apertures to provide a dispersed blend; and collecting the dispersed blend as a mat on a fiber collector to provide a mat comprising pills of balled-up cellulosic and synthetic fibers wherein portions of the fibers of the pills extend in an upward direction relative to the plane of the mat;

wherein the fiberizing and blending steps occur simultaneously in a blending and fiberizing chamber.

8. A method of forming a mat of cellulosic fibers and synthetic fibers, comprising the steps of:

fiberizing cellulosic material into cellulosic fibers;

dispersing the fiberized cellulosic fibers through a fiber disperser having apertures to provide dispersed cellulosic fibers;

injecting a metered amount of synthetic fibers into the dispersed cellulosic fibers to blend the cellulosic fibers with the metered amount of synthetic fibers to form a fiber blend; and collecting the fiber blend as a mat on a fiber collector to provide a mat comprising pills of balled-up cellulosic and synthetic fibers wherein portions of the fibers of the pills extend in an upward direction relative to the plane of the mat.

* * * * *